US006894026B1

(12) United States Patent
Quay

(10) Patent No.: US 6,894,026 B1
(45) Date of Patent: May 17, 2005

(54) LONG-ACTING OXYTOCIN ANALOGUES FOR THE TREATMENT AND PREVENTION OF BREAST CANCER AND PSYCHIATRIC DISORDERS

(75) Inventor: Steven C. Quay, Edmonds, WA (US)

(73) Assignee: Atossa Healthcare, Inc., Bothell, WA (US)

( * ) Notice: Subject to any disclaimer, the term of this patent is extended or adjusted under 35 U.S.C. 154(b) by 204 days.

(21) Appl. No.: 09/678,591

(22) Filed: Oct. 3, 2000

Related U.S. Application Data

(63) Continuation-in-part of application No. 09/481,058, filed on Jan. 11, 2000, now abandoned.

(51) Int. Cl.[7] .............................................. A61K 38/00
(52) U.S. Cl. ................................ 514/9; 514/2; 514/11
(58) Field of Search ........................................ 514/9, 2

(56) References Cited

U.S. PATENT DOCUMENTS

| | | | |
|---|---|---|---|
| 5,482,931 A | * | 1/1996 | Harris et al. ................... 514/15 |
| 5,798,266 A | | 8/1998 | Quay et al. |
| 6,333,313 B1 | * | 12/2001 | Copland et al. ............... 514/12 |

FOREIGN PATENT DOCUMENTS

| | | |
|---|---|---|
| WO | 88/09810 | 12/1988 |
| WO | 89/10134 | 11/1989 |
| WO | 98/08976 | 3/1998 |

OTHER PUBLICATIONS

Cassoni, P. et al.., "Oxytonin inhibits proliferation of human breast cancer cell lines", Virchows Archive. 425:467–472, 1994.*
Lipton, A. et al., "Acute inhibition of rat myometrial responses to oxytocin by tamoxifen stereoisomers and oestradiol", J. Endocr. 103, 383–388, 1984.*
Stein, J., editor–in–chief, Internal Medicine, 4th Edition, Chapters 71–72, pp. 699–715, 1994.*
Boer et al., "Oxytocin in Obsessive Compulsive Disorder", Peptides, vol. 13, pp. 1083–1085, 1992.*
Leckman, J. F. et al., "The Role of Central Oxytocin in Obsessive Compulsive Disorder and Related Normal Behavior", Psychoneuroendocrinology, vol. 19, No. 8, pp. 723–749, 1994.*
Windholz, M. et al., Editor–in–Chief, The Merck Index, An Encyclopedia of Chemicals, Drugs, and Biologicals, 10th Edition, p. 1300, 1986.*
Windholz, M., Editor, The Merck Index, An Encyclopedia of Chemicals, Drugs, and Biologicals, 10th Edition, Compound No 8923, p. 1300, Jul. 21, 1986.*
Altemus et al., "Normal CSF Oxytocin and NPY Levels in OCD," Biol. Psychiatry 45: 931–33, 1999.
Cassoni et al., "Oxytocin Inhibits Proliferation of Human Breast cancer Cell Lines," Virchows Archiv. 425:467–472, 1994.

Cassoni et al., "Oxytocin and Oxytocin–Analogue F314 Inhibit cell Proliferation and Tumor Growth of Rat and Mouse mammary carcinomas," Int. J. Cancer 66:817–820, 1996.
Cassoni et al., "Oxytocin Inhibits the Proliferation of MDA–MB231 Human Breast–Cancer Cells Via Cyclic Adenosine Monophosphate and Protein Kinase A," Int. J. Cancer 72:340–344, 1997.
den Boer and Westenberg, "Oxytocin in Obsessive Compulsive Disorder," Peptides 13:1083–85, 1992.
Insel et al., "Oxytocin, Vasopressin, and Autism: Is There a Connection?," Biol. Psychiatry 45:145–157, 1999.
Leckman et al., "The Role of Central Oxytocin in Obsessive Compulsive Disorder and Related Normal Behavior," Psychoneuroendocrinology 19:723–749, 1994.
Leckman et al., "Elevated Cerebrospinal Fluid Levels of Oxytocin in Obsessive–compulsive Disorder,"Arch Gen Psychiatry 51:782–92, 1994.
Lipton et al., "Acute Inhibition of Rat Myometrial Responses to Oxytocin by Tamoxifen Stereoisomers and Oestradiol," J. Endocr. 103:383–388, 1984.
Martin et al., "Cerebrospinal Fluid Levels of Oxytocin in Prader–Willi Syndrome: A Preliminary Report," Biol. Psychiatric 44:1349–1352, 1998.
Modahl et al., "Plasma Oxytocin Levels in Autistic Children," Biol. Psychiatric 43 :270–277, 1998.
Atke et al., "Uterotonic Activity and Myometrial Receptor Affinity of 1–Deamino–1–Carwba–2–Tyrosine (O–Methyl)–Oxytocin," Acta Endocrinol. 115:155–160, 1987.

(Continued)

Primary Examiner—Dwayne Jones
(74) Attorney, Agent, or Firm—Graybeal Jackson Haley LLP

(57) ABSTRACT

Methods and compositions are provided for prophylaxis and treatment of breast cancer involving administration of a therapeutically effective amount of carbetocin and/or other long-acting oxytocin analogues. 1-Butanoic acid-2-(O-methyl-L-tyrosine)-1-carbaoxytocin (carbetocin) and/or other long-acting oxytocin analogues are formulated with a pharmaceutically acceptable carrier and administered in an amount sufficient to inhibit initiation or growth of breast cancer in the patient. The carbetocin and/or other long-acting oxytocin analogues may also be formulated with a pharmaceutically acceptable carrier and administered in an amount sufficient to treat, prevent or alleviate the symptoms of a psychiatric disorder in the patient. Carbetocin may be administered prophylactically or to treat existing conditions in patients by a variety of administration modes, including intramuscular, intravenous, intranasal, intrapulmonary, subcutaneous, parenteral, oral, or transdermal delivery methods and formulations. Preferably, the carbetocin is administered to a mucosal surface of the patient via intranasal delivery. For this purpose, pharmaceutical compositions are provided for intranasal delivery that incorporate carbetocin in a powder or aqueous formulation for intranasal delivery.

11 Claims, No Drawings

OTHER PUBLICATIONS

Boucher et al., "Double–Blind, Randomized Comparison of the Effect of Carbetocin and Oxytocin on Intraoperative Blood Loss and Uterine Tone of Patients Undergoing Cesarean Section," *J. Perinatology* 18:202–207, 1998.

Bussolati et al., "Immunolocalization and Gene Expression of Oxytocin Receptors in Carcinomas and Non–Neoplastic Tissues of the Breast," *Am. J. Pathol.* 148:1895–1903, 1996.

Cobo, E., "Characteristics of the Spontaneous Milk Ejecting Activity Occurring During Human Lactation," *J. Perinat. Med.* 21:77–85, 1993.

Cort et al., "Effect of Oxytocin and its Long–Acting Analog on Milk Let–down and Intramammary Pressure in Healthy Lactating Sows," *Am. J. Vet. Res.* 43:1283–1285, 1982.

Dansereau et al., "Double–Blind Comparison of Carbetocin Versus Oxytocin in Prevention of Uterine Atony After Cesarean Section," *AM. J. Obstet. Gynecol.* 180:670–676, 1999.

Engstrom et al., "Oxzytocin Receptor Binding and Uterotonic Activity of Carbetocin and Its Metabolites Following Enzymatic Degradation," *Eur. J. Pharmacol.* 355:203–210, 1998.

Fay et al., "Oxytocin Does Not Induce A Rise in Intracellular Free Calcium in Human Breast Cancer Cells," *Res. Commun. Mol. Pathol. Pharmacol.* 103:115–128, 1999.

Gonser, M., "Labor Induction and Augmentation with Oxytocin: Pharmacokinetic Considerations," *Arch. Gynecol. Obstet.* 256:63–66, 1995.

Hunter et al.m "Effect of Carbetocin, A Long–Acting Oxytocin Analog on the Postpartum Uterus," *Clin. Pharmacol. Ther.* 52:60–67, 1992.

Ito et al., "Investigation of the Oxytocin Recptor Expression in Human Breast Cancer Tissue Using Newly Established Monoclonal Antibodies," *Endocrinology* 137:773–779, 1996.

Kimura et al., "Expression and Immunolocalization of the Oxytocin Receptor in Human Lactating and Non–Lactating Mammary Glands," *Human Reprod.* 13: 2645–2653, 1998.

Mena, F., "Central Effects of Catecholamines Upon Mammary Contractility in Rats Are Neurally Mediated," *Neuroendocrinology* 61:722–730, 1995.

Murrell, T.G.C. "The Potential for Oxytocin (OT) to Prevent Breast Cancer: A Hypothesis," *Breast Cancer Res. Treat.* 35:225–229, 1995.

Murrell, "Epidemiological and Biochemical Support for a Theory on the Causes and Prevention of Breast Cancer," *Med. Hypotheses* 36:389–396, 1991.

Nass et al., "The Biology of Breast Cancer," *Hematol. Oncol. North Am.* 13:311–332, 1999.

Newton, N., "The Quantitative Effect of Oxytocin (Pitocin) on Human Milk Yield," *Ann. N.Y. Acad. Sci.* 652:481–483.

Norström et al.,k "Contractile Effect of Oxytocin and 1–Deamino–1–Carba–2–Tyrosine (0–Methyl)–Oxytocin in Myometrial Tissue from Non–Pregnant and Term Pregnant Women," *Acta Endocrinol.* 122:566–568, 1990.

Orhue, A., "Incremental Increases in Oxytocin Infusion Regimens for Induction of Labor at Term in Primigravidas: A Randomized Controlled Trial," *Obstet. Gynecol.* 83:229–233, 1994.

Planchon et al., "Alteration of Prostaglandin E Receptors in Advanced Breast Tumor Cell Lines," *Mol. Cell. Endocrinol.* 111:219–233, 1995.

Sapino et al., "Oxytocin Receptor Within the Breast: Biological Function and Distribution," *Anticancer Res.* 18:2181–2186, 1998.

Sapino et al., "Oxytocin Enhance Myoepithelial Cell Differentiation and Proliferation in the Mouse Mammary Gland," *Endocrinology* 133:838–842, 1993.

Satin et al., "Factors Affecting the Dose Response to Oxytocin for Labor Stimulation," *Am. J. Obstetl. Gynecol.* 166:1260–1261, 1992.

Satin et al., "High–Dose Oxytocin" 20–Versus 40–Minute Dosage Interval, *Obstet. Gynecol.83*: 234–238, 1994.

Silcox, et al., "Transfer of Carbetocin into Human Breast Milk," *Obstet. Gynecol.* 82:456–459, 1993.

Taylor et al., "Interaction of Vasopressin and Oxytocin with Human Breast Carcinoma Cells," *Cancer Res.* 50:7882–7886, 1990.

Van Dongen et al., "Ascending Dose Tolerance Study of Intramuscular Carbetocin Administered After Normal Vaginal Birth," *Eur. J. Obstet. Gynecol. Reprod. Biol.* 77:181–187, 1998.

Vilhardt et al., "Interaction of Chymotrypsin with Carbetocin ([1–Deamino–1–Monocarba–2–O–Methyltyrosine]–Oxytocin)," *Pharmacol. Toxicol.* 81:147–150, 1997.

\* cited by examiner

LONG-ACTING OXYTOCIN ANALOGUES FOR THE TREATMENT AND PREVENTION OF BREAST CANCER AND PSYCHIATRIC DISORDERS

CROSS-REFERENCES TO RELATED APPLICATIONS

This application is a continuation-in-part of U.S. patent application Ser. No. 09/481,058, filed Jan. 11, 2000 now abandoned.

BACKGROUND OF THE INVENTION

Breast cancer is the most common form of cancer in women, resulting in approximately 180,000 new cancer cases annually and causing 18% of cancer-related deaths of women in the United States. It is the second leading cause of cancer-related deaths in humans. Despite recent advances in diagnosing and treating breast cancer, the incidence of this disease has steadily risen at a rate of about 1% per year since 1940. It is estimated that a total of 183,400 new patients were diagnosed with breast cancer in 1995, of which 46,240 will die of the disease. Today, the likelihood that a woman living in North America will develop breast cancer during her lifetime is one in eight.

In light of these statistics, efforts to develop new, more effective methods for treating breast cancer have long been of paramount importance in the medical and research communities. Nevertheless, current methods for treating breast cancer remain limited primarily to conventional surgery, radiation treatment and chemotherapy. These treatment methods are frequently insufficient to prevent progression or recurrence of the disease, and are each attended by severe side effects.

In the case of chemotherapy, many compounds have been shown to be effective against cancerous cells. However, the exact mechanisms of action of many chemotherapeutic agents remain unknown, and these agents often incidentally harm or destroy normal cells. In addition, cytocidal and cytostatic agents work best on cancers with large growth indices, i.e., ones whose cells are rapidly dividing. Thus, chemotherapeutic approaches may be less successful against cancers that are pre-metastatic or that are not particularly aggressive in their growth. Moreover, while some chemotherapeutic agents may reduce a tumor mass significantly after one treatment, they may not be amenable to repeated administration to the same patient if the tumor returns, as is usually the case. Some chemotherapeutic agents can only be administered once in a lifetime, while others require several months or years between treatments. Finally, most become ineffective due to the development of multi-drug resistance by the tumors.

In view of these drawbacks associated with conventional chemotherapy, greater attention in the medical and research communities has been drawn toward developing hormonal therapy agents for treating or preventing breast cancer. One promising class of agents in this context, which has now become a widely used and effective tool against breast cancer, is the anti-estrogen compounds tamoxifen and raloxifene. Tamoxifen and raloxifene belong to a class of pharmaceutical agents termed selective estrogen receptor inhibitors (SERIs). About two thirds of breast tumors express the estrogen receptor-α (ER). Many of these ER positive tumors appear dependent on estrogen for growth and survival, and thus may respond to treatment with anti-estrogens. Tamoxifen has proven to be a successful treatment agent in this context. Unfortunately, the remaining one third of breast cancers which are ER-negative at the time of diagnosis generally do not respond to endocrine therapy. In addition, acquired resistance to tamoxifen in ER-positive tumors is common. For these patients, there is clearly a need for new and better treatment options.

Ideally, new therapeutic and prophylactic agents against breast cancer will target important biological pathways in breast cell growth and differentiation. With respect to developing new hormonal treatment strategies, a large number and variety of hormones and growth factors are thought to interact in complex pathways to influence breast cancer initiation and disease progression. Examples of hormonal regulatory factors that may be involved in such interactions include somatostatin, mammostatin, vasopressin, mammary-derived growth inhibitor (MDGI), mammary-derived growth factor-1 (MDGF-1), inhibins, activins, androgens, glucocorticoids, vitamin D, thyroid hormones, ecosinoids, and oxytocin. However, the contributions of these diverse hormones and growth factors to the initiation and progression of breast cancer remain poorly understood. Even the relatively well known effects of estrogens and anti-estrogens on breast cells appear to depend on interactions among a variety of agents and pathways. These interactions may vary significantly among individual breast tumors, for example depending on genetic or environmental variables such as oncogene activation or the presence or absence of tumor suppressors. Accordingly, a better understanding of how cancer cells circumvent their dependency on normal growth and developmental signals and pathways is of paramount interest.

Among the many hormonal regulatory factors that have been investigated as possible tools for regulating breast cell growth, differentiation and/or survival, the peptide hormone oxytocin has received recent interest as a potential growth modulating agent for breast cancer cells. Human breast cancer cell lines and biopsy samples have been reported to express the oxytocin receptor (OR), as have normal breast myoepithelial and epithelial cells and intraductal cells in benign hyperplastic lesions (Taylor et al., *Cancer Res.* 50:7882–7886, 1990; Cassoni et al., *Virchows Archiv.* 425:467–472, 1994; Bussolati et al., *Am. J. Pathol.* 148:1895–1903, 1995; Planchon et al., *Mol. Cell. Endocrinol.* 111:219–223, 1995; Ito et al., *Endocrinology* 137:773–779, 1996; Kimura et al., *Human Reprod.* 13:2645–2653, 1998; Sapino et al., *Anticancer Res.* 18:2181–2186, 1998). Several of these and related reports suggest that oxytocin can modulate growth and/or differentiation of breast cancer cells (Taylor et al., *Cancer Res.* 50:7882–7886, 1990; Cassoni et al., *Virchows Archiv.* 425:467–472, 1994; Cassoni et al., *Int. J. Cancer* 66:817–820, 1996; Cassoni et al., *Int. J. Cancer* 72:340–344, 1997; Sapino et al., *Anticancer Res.* 18:2181–2186, 1998).

In one study, oxytocin was reported to inhibit proliferation of undifferentiated stem cells in the mouse mammary gland, while increasing the relative number of differentiated myoepithelial and epithelial cells (Sapino et al., *Endocrinology* 133:838–842, 1993). In another study, the effects of oxytocin and an oxytocin analog, F314, were investigated on cell cultures and xenographs of mouse mammary and colon carcinomas and rat mammary carcinoma (Cassoni et al., *Int. J. Cancer* 66:817–820, 1996). Both cell proliferation and tumor growth were reportedly inhibited by oxytocin and F314. Additional reports by the same research group concluded that oxytocin inhibits proliferation of human hormone-dependent MCF7 and hormone-independent MDA-MB231 breast cancer cells in vitro and enhances the known inhibitory effect of tamoxifen on estrogen-dependent MCF7 cells and TS/A (Cassoni et al., *Virchows Archiv.* 425:467–472, 1994; Cassoni et al., *Int J. Cancer* 66:817–820, 1996; Cassoni et al., *Int. J. Cancer* 72:340–344, 1997; Sapino et al., *Anticancer Res.* 18:2181–86, 1998). Based on the accumulated data from these reports, the authors propose that oxytocin may mediate a spectrum of different cellular responses, in different signal-transduction systems, in cells with different phenotypes, and in combination with other mammotrophic hormones through yet undefined mechanisms and pathways.

In view of these reports, there remains a great deal of uncertainty concerning the possible effects of oxytocin and other hormonal regulatory factors on breast cell growth, differentiation and survival. This uncertainty is underscored by a number of conflicting reports about the nature and activity of oxytocin as a regulatory factor in breast cell development. For example, Taylor et al., *Cancer Res.* 50:7882–7886, 1990, report that oxytocin is mitogenic for estrogen-dependent MCF7 cells—an opposite conclusion to that rendered by the Cassoni research group in the series of reports discussed above. The mitogenic activity of oxytocin observed by Taylor and coworkers was shared by another peptide hormone, vasopressin. However, vasopressin was observed to be mitogenic for MCF7 cells only at low doses, and to exert an opposite, anti-proliferative effect on these same cells at higher doses. In a separate report Sapino et al. (*Anticancer Res.* 18:2181–86, 1998) state that oxytocin exerts an independent "trophic effect" on breast myoepithelial cells that induces their proliferation and differentiation. In yet another conflicting study, Ito and coworkers (*Endocrinology* 137:773–779, 1996) report that "the effects of OT (oxytocin) on the growth of cultures breast cancer cells are inconsistent in the short term", and that available data suggest "that OT does not influence the morphological differentiation of the cancer cell. These collective reports provide insufficient insight and guidance regarding the potential utility of oxytocin, oxytocin analogs, and other hormonal factors as therapeutic agents for successful prophylaxis and treatment of breast cancer.

Whereas the role of oxytocin in breast cell development remains largely undefined, this peptide hormone has well characterized activities for stimulating milk let-down and inducing uterine contraction in mammalian subjects (see, e.g., Boucher et al., *J. Perinatology* 18:202–207, 1998; Cort et al., *Am. J. Vet. Res.* 43:1283–1285, 1982). In the clinical setting, oxytocin is routinely used as a labor-inducing agent and during postpartum care or cesarean section to prevent uterine atony and to control bleeding or hemorrhage after delivery of the placenta. It is also widely used as a treatment agent to enhance milk letdown in lactating patients, which activity involves stimulation of contraction by myoepithelial cells surrounding the mammary alveoli. Because oxytocin has a relatively short half-life of only about 4 to 10 minutes in the human system, it must generally be administered by continuous intravenous (IV) infusion to achieve desired uterotonic and milk let-down effects (Boucher et al., *J. Perinatology* 18:202–207, 1998). However, long-term, repeated or high dose administrations of oxytocin may be attended by substantial side effects.

Oxytocin has also been implicated as a potential factor in certain psychiatric disorders. For example, based on a review of evidence from animal studies demonstrating that the nonapeptides, oxytocin and vasopressin, have unique effects on the normal expression of species-typical social behavior, communication and rituals, Insel and colleagues have proposed that oxytocin or vasopressin neurotransmission may account for several features associated with autism. (Inset et al., *Biol. Psychiatry* 45:145–157, 1999). A study on autistic children reported that such children had significantly lower levels of plasma oxytocin than normal children. Elevated oxytocin levels were associated with higher scores on social and developmental tests in non-autistic children, but associated with lower scores in autistic children, suggesting that altered oxytocin levels may be associated with autism in children (Modahl et al., *Biol. Psychiatric* 43:270–277, 1998). A role for oxytocin in obsessive compulsive disorders has also been proposed (Leckman et al., *Psychoneuroendocrinology* 19:723–749, 1994; but see Altemus et al., *Biol. Psychiatry* 45:931–33, 1999). In particular, elevated levels of oxytocin have been proposed to affect certain obsessive-compulsive behaviors, such as excessive worrying, sexual compulsions and/or compulsive washing and cleaning. (Leckman et al., *Psychoneuroendocrinology* 19:723–749, 1994; Leckman et al., *Arch Gen Psychiatry* 51:782–92, 1994). Elevated levels of oxytocin have also been implicated in Prader-Willi syndrome, a genetic disorder associated with mental retardation, appetite dysregulation and a risk of developing obsessive compulsive disorder (Martin et al., *Biol. Psychiatric* 44:1349–1352, 1998). One study found that intranasal administration of oxytocin was not effective, however, as an anticompulsive agent (den Boer and Westenberg, *Peptides* 13:1083–85, 1992).

A number of oxytocin analogs have been evaluated as possible substitute agents for inducing uterine contraction and milk let-down in mammalian patients with the goal of minimizing oxytocin's side effects. One such analog, carbetocin (1-butanoic acid-2-(O-methyl-L-tyrosine)-1-carbaoxytocin, or, alternatively, deamino-1 monocarba-(2-O-methyltyrosine)-oxytocin [d(COMOT)]) is a long-acting synthetic oxytocin analog which exhibits both utcrotonic and milk let-down inducing activities (Atke et al., *Acta Endocrinol.* 115:155–160, 1987; Norstrom et al.,*Acta Endocrinol.* 122:566–568, 1990; Hunter et al., *Clin. Pharmacol. Ther.* 52:60–67, 1992; Silcox et al., *Obstet Gynecol.* 82:456–459, 1993; Vilhardt et al., *Pharmacol. Toxicol.* 81:147–150, 1997; Boucher et al., *J. Perinatology* 18:202–207, 1998). The half-life of carbetocin is reportedly 4 to 10 times longer than that of oxytocin, which is reflected in substantial prolongation of the uterotonic and milk let-down inducing activities of this analog. This apparent increase in metabolic stability is attributed to N-terminal desamination and replacement of a 1–6 disulfide bridge by a methylene group in carbetocin, which modifications are thought to protect this analog from aminopeptidase and disulfidase cleavage (Hunter et al., *Clin. Pharmacol. Ther.* 52:60–67, 1992).

Despite these apparent advantages of carbetocin over its parent molecule oxytocin, it is widely noted that modifications of peptides and proteins can substantially reduce or even abolish biological activities in the modified analog (see, e.g., Vilhardt et al., *Pharmacol. Toxicol.* 81:147–150, 1997). This appears to be at least partially the case for carbetocin, based on reports that the potency of this analog is reduced in vivo to as little as one-tenth the potency of native oxytocin (Hunter et al., *Clin. Pharmacol. Ther.* 52:60–67, 1992). Another potential drawback to using peptide analogs such as carbetocin is that, in addition to having diminished potency, they may also act as antagonists to inhibit activities of their native counterparts (e.g., by competitive binding with a target receptor). In this context, reports suggest that carbetocin, while exhibiting some degree of agonist activity, also acts as an antagonist against native oxytocin (Engstrom et al., *Eur. J. Pharmacol.* 355:203–210, 1998). Yet another concern for using peptide analogs relates to their potential side effects. In the case of carbetocin, dose acceleration studies have revealed significant toxicity of this analog in clinical settings (van Dongen, *Eur. J. Obstet. Ganecol. Reprod. Biol.* 77:181–187, 1998). Among 45 women who received between 15 µg–200 µg of carbetocin by intramuscular injection within 24 hours of childbirth, seven women suffered serious adverse side effects. Six cases presented with blood loss of at least 1000 ml. Four cases required manual placenta removal. Five cases required additional oxytocics administration and five required blood transfusion.

In view of the foregoing, there remains an urgent need in the art for novel tools and methods to manage and treat breast cancer, psychiatric disorders and other conditions in which abnormal oxytocin levels are implicated. In particular, new biological targets must be ascertained and novel therapies designed to manage and treat breast cancers that are not subject to treatment by conventional chemotherapeutic methods or anti-estrogen therapies. Such new agents could be used alone or in combination with chemotherapy or anti-estrogen treatment to improve patient outcomes. Similarly, new biological agents must be developed to manage and treat psychiatric disorders that are not subject to treatment by conventional therapies. Such new agents could be used alone or in combination with existing drug regimens to improve patient outcomes. Surprisingly, the methods and compositions of the present invention fulfill these needs and satisfy other objects and advantages that will become apparent from the description which follows.

SUMMARY OF THE INVENTION

The instant invention provides novel methods and compositions for preventing, delaying the onset of, and treating both clinical breast cancer, occult breast cancer, and psychiatric disorders in mammals, including humans. The methods of the invention involve administering a therapeutically effective amount of carbetocin and/or other long-acting oxytocin analogues to a patient suffering from breast cancer, or a psychiatric disorder, or presenting with an elevated risk for developing such disease or disorder. The novel formulations include carbetocin and/or other long-acting oxytocin analogues in a pharmaceutically acceptable carrier and are administered in an amount sufficient to treat the disease or disorder (e.g., to inhibit initiation or growth of breast cancer, or to reduce the symptoms associated with a psychiatric disorder).

According to the methods of the invention, carbetocin and/or other long-acting oxytocin analogues may be administered to subject patients by a variety of administration modes, including intramuscular, intravenous, intranasal, intrapulmonary, subcutaneous, parenteral, oral, or transdermal delivery methods and formulations. In preferred embodiments, carbetocin is administered to a mucosal surface of the patient, e.g., via intrapulmonary or intranasal delivery. In more detailed aspects of the invention, novel pharmaceutical compositions are provided for intranasal delivery that incorporate carbetocin and/or other long-acting oxytocin analogues in formulations for intranasal delivery.

For prophylactic and treatment purposes, carbetocin and/ or other long-acting oxytocin analogues may be administered to the patient in a single bolus injection delivery protocol, via continuous IV or transdermal delivery over an extended time period, or in a repeated administration protocol (e.g., on a daily or weekly basis). In preferred embodiments, carbetocin is self-administered by the patient daily as an intranasal spray or powder formulation. The various dosages and delivery protocols thus contemplated for administration of carbetocin are therapeutically effective to inhibit the occurrence or recurrence of breast cancer in the patient, to alleviate one or more symptoms of existing breast cancer in a patient, or to treat or alleviate the symptoms of a psychiatric disorder. To treat existing breast cancer, carbetocin may be employed within the methods of the invention to inhibit growth or metastatic progression of existing breast tumors.

In yet additional aspects of the invention, carbetocin and/or another long-acting oxytocin analogue is administered according to the foregoing methods in a coordinate treatment or prophylaxis protocol with another anti-breast cancer agent, such as a hormonal or chemotherapeutic treatment agent. In one embodiment, carbetocin is administered coordinately with an anti-estrogen compound, e.g., tamoxifen or raloxifen, to prevent or treat breast cancer in a patient suffering from, or at risk of developing, the disease. Carbetocin is administered as above, simultaneously or sequentially with administration of tamoxifen or raloxifen, the latter of which are administered in amounts sufficient to independently inhibit initiation or growth of estrogen-dependent breast cancer in the patient.

In other aspects of the invention, carbetocin and/or another long-acting oxytocin analogue is administered according to the foregoing methods in a coordinate treatment or prophylaxis protocol with an antidepressant, such as a selective serotonin reuptake inhibitor (SSRI) or serotonin reuptake inhibitor (SRI). In one embodiment, carbetocin is administered coordinately with an SSRI (e.g., fluvoxamine, paroxetine, sertraline or fluoxetine), or an SRI (e.g., clomipramine) to prevent, treat or alleviate the symptoms of a psychiatric disorder, such as obsessive compulsive disorder, autism or Prader-Willi syndrome. In another embodiment, carbetocin is administered simultaneously or sequentially with administration of an SSRI in amounts sufficient to treat, prevent or alleviate the symptoms of the psychiatric disorder in the patient.

Also provided within the invention are pharmaceutical compositions for use within the methods of the invention for prophylaxis or treatment of breast cancer. These compositions include a therapeutically effective amount of carbetocin and/or other long-acting oxytocin analogue sufficient to inhibit initiation or growth of breast cancer in a mammalian patient and formulated in a pharmaceutically acceptable carrier. Similarly, pharmaceutical compositions are also provided for use within the methods of the invention for prophylaxis or treatment of psychiatric disorders. These compositions include a therapeutically effective amount of carbetocin and/or other long-acting oxytocin analogue. Such amounts are typically sufficient to inhibit initiation or growth of breast cancer in a mammalian patient, or to treat or prevent the symptoms of a psychiatric disorder. The compositions are typically formulated in a pharmaceutically acceptable carrier. In preferred embodiments, carbetocin is formulated in a carrier for intranasal or intrapulmonary administration. Intranasal formulations are provided as aqueous solutions or suspensions or powders for intranasal delivery as an aerosol or propelled particulate bolus to facilitate administration and enhance delivery. Various excipients, stabilizers absorption enhancers and other additives are optionally provided to optimize shelf-life, delivery and efficacy and to minimize irritation and other adverse side effects.

DESCRIPTION OF THE SPECIFIC EMBODIMENTS

The methods and compositions of the invention are useful for prophylaxis of breast cancer in mammalian patients at high risk for developing the disease, as well as for treatment of patients presenting with existing breast cancer. Subject patients for prophylactic therapy according to the methods of the invention include peri-menopausal women, women over twenty who have a family history of breast cancer, and women who test positive in a breast cancer screen designed to detect early breast cancer markers indicating elevated risk for development of the disease. Subject patients for treatment according to the methods of the invention include males and females diagnosed with existing breast cancer, or patients who have been treated for known breast cancer and thus present an elevated risk of disease recurrence. Breast cancer treatment and prevention employing the methods and compositions of the invention may be implemented as an independent treatment program or as a follow-up, adjunct or coordinate treatment regimen to breast cancer surgery, chemotherapy or hormonal treatment.

To facilitate identification of patients for which carbetocin treatment according to the invention is indicated, a variety of screening methods are known and widely used in the art. Patients presenting with existing breast cancer may be identified by conventional mammographic and biopsy techniques. To identify patients at elevated risk for developing breast cancer, a variety of screening methods are available. Recent efforts to develop improved methods for breast cancer detection, staging and classification have focused on a promising array of so-called cancer "markers." Cancer markers are typically proteins that are uniquely expressed (e.g. as a cell surface or secreted protein) by cancerous cells, or are expressed at measurably increased or decreased levels by cancerous cells compared to normal cells. Other cancer markers can include specific DNA or RNA sequences marking deleterious genetic changes or alterations in the patterns or levels of gene expression associated with particular forms of cancer.

A large number and variety of breast cancer markers have now been identified, and many of these have been shown to have important value for determining prognostic and/or treatment-related breast cancer variables. Prognostic variables are those variables that serve to predict disease outcome, such as the likelihood or timing of relapse or survival. Treatment-related variables predict the likelihood of success or failure of a given therapeutic plan. Certain breast cancer markers clearly serve both functions. For example, estrogen receptor levels are predictive of relapse and survival for breast cancer patients, independent of treatment, and are also predictive of responsiveness to endocrine therapy. Pertschuk et al., *Cancer* 66: 1663–1670, 1990; Parl and Posey, *Hum. Pathol.* 19: 960–966, 1988; Kinsel et al., *Cancer Res.* 49: 1052–1056, 1989; Anderson and Poulson, *Cancer* 65: 1901–1908, 1989.

The utility of specific breast cancer markers for screening and diagnosis, staging and classification, monitoring and/or therapy purposes depends on the nature and activity of the marker in question. For general reviews of breast cancer markers, see Porter-Jordan et al., *Hematol. Oncol. Clin. North Amer.* 8: 73–100, 1994; and Greiner, *Pharmaceutical Tech., May,* 1993, pp. 28–44. As reflected in these reviews, a primary focus for developing breast cancer markers has centered on the overlapping areas of tumorigenesis, tumor growth and cancer invasion. Tumorigenesis and tumor growth can be assessed using a variety of cell proliferation markers (for example Ki67, cyclin D1 and proliferating cell nuclear antigen (PCNA)), some of which may be important oncogenes as well. Tumor growth can also be evaluated using a variety of growth factor and hormone markers (for example estrogen, epidermal growth factor (EGF), erbB-2, transforming growth factor (TGF), which may be overexpressed, underexpressed or exhibit altered activity in cancer cells. By the same token, receptors of autocrine or exocrine growth factors and hormones (for example insulin growth factor (IGF) receptors, and EGF receptor) may also exhibit changes in expression or activity associated with tumor growth. Lastly, tumor growth is supported by angiogenesis involving the elaboration and growth of new blood vessels and the concomitant expression of angiogenic factors that can serve as markers for tumorigenesis and tumor growth.

In addition to tumorigenic, proliferation and growth markers, a number of markers have been identified that can serve as indicators of invasiveness and/or metastatic potential in a population of cancer cells. These markers generally reflect altered interactions between cancer cells and their surrounding microenvironment. For example, when cancer cells invade or metastasize, detectable changes may occur in the expression or activity of cell adhesion or motility factors, examples of which include the cancer markers Cathepsin D, plasminogen activators, collagenases and other factors. In addition, decreased expression or over-expression of several putative tumor "suppressor" genes (for example nm23, p53 and rb) has been directly associated with increased metastatic potential or deregulation of growth predictive of poor disease outcome.

In summary, the evaluation of proliferation markers, oncogenes, growth factors and growth factor receptors, angiogenic factors, proteases, adhesion factors and tumor suppressor genes, among other cancer markers, can provide important information concerning the risk, presence, status or future behavior of cancer in a patient. Determining the presence or level of expression or activity of one or more of these cancer markers can aid in the differential diagnosis of patients with uncertain clinical abnormalities, for example by distinguishing malignant from benign abnormalities. Furthermore, in patients presenting with established malignancy, cancer markers can be useful to predict the risk of future relapse, or the likelihood of response in a particular patient to a selected therapeutic course. Even more specific information can be obtained by analyzing highly specific cancer markers, or combinations of markers, which may predict responsiveness of a patient to specific drugs or treatment options.

Methods for detecting and measuring cancer markers have been recently revolutionized by the development of immunological assays, particularly by assays that utilize monoclonal antibody technology. Previously, many cancer markers could only be detected or measured using conventional biochemical assay methods, which generally require large test samples and are therefore unsuitable in most clinical applications. In contrast, modern immunoassay techniques can detect and measure cancer markers in relatively much smaller samples, particularly when monoclonal antibodies that specifically recognize a targeted marker protein are used. Accordingly, it is now routine to assay for the presence or absence, level, or activity of selected cancer markers by immunohistochemically staining breast tissue specimens obtained via conventional biopsy methods. Because of the highly sensitive nature of immunohistochemical staining, these methods have also been successfully employed to detect and measure cancer markers in smaller, needle biopsy specimens which require less invasive sample gathering procedures compared to conventional biopsy specimens. In addition, other immunological methods have been developed and are now well known in the art which allow for detection and measurement of cancer markers in non-cellular samples such as serum and other biological fluids from patients. The use of these alternative sample sources substantially reduces the morbidity and costs of assays compared to procedures employing conventional biopsy samples, which allows for application of cancer marker assays in early screening and low risk monitoring programs where invasive biopsy procedures are not indicated.

For the purpose of breast cancer evaluation to predict the efficacy of carbetocin treatment according to the instant invention, the use of conventional or needle biopsy samples for cancer marker assays is often undesirable. This is because a primary goal of such assays is to detect the cancer before it progresses to a palpable or mammographically detectable tumor stage. Prior to this stage, biopsies are generally contraindicated, making early screening and low risk monitoring procedures employing such samples untenable. Therefore, it is preferable to obtain samples for breast cancer marker assays by less invasive means than biopsy, for example by serum withdrawal. However, efforts to utilize serum samples for breast cancer marker assays have met with limited success, largely because the targeted markers are either not detectable in serum, or because telltale changes in the levels or activity of the markers cannot be monitored in serum. In addition, the presence of breast cancer markers in serum probably occurs at the time of micro-metastasis, making serum assays less useful for detecting pre-metastatic disease.

In contrast, fluid samples within the mammary glands themselves are expected to contain much higher and more biologically relevant levels of breast cancer markers than serum, particularly in view of the fact that 80%–90% of all breast cancers occur within the intraductal epithelium of these glands. Fluid within the breast ducts is expected to contain an assemblage and concentration of hormones, growth factors and other potential markers comparable to those secreted by, or acting upon, the surrounding cells of the alveolar-ductal system. Likewise, mammary fluid is expected to contain cells and solid cellular debris or products that can be used in cytological or immunological assays to evaluate intracellular or cell surface markers that may not be detectable in the liquid fraction of mammary fluid.

Recently, powerful new technology has been developed that allows for non-invasive breast cancer marker assays to be conducted utilizing oxytocin-induced mammary fluid samples. In particular, U.S. Pat. No. 5,7998,266 issued to Quay et al. on Aug. 25, 1998; U.S. patent application Ser. No. 09/027,362 filed by Quay et al. on Feb. 20, 1998; and U.S. patent application Ser. No. 09/435,131, filed by Quay et al. Nov. 5, 1999 (each incorporated herein by reference) provide non-invasive methods, kits and devices for obtaining biological samples of breast fluid and for employing these samples in methods and compositions to evaluate, diagnose and facilitate management of breast diseases, including breast cancer. These methods, kits and devices employ, or may be used in conjunction with, artificial stimulation of breast fluid expression by administration of oxytocin, or an oxytocin analog or by application of a novel breast fluid sample collection device, alone or in conjunction with oxytocin stimulation.

More specifically, the above-incorporated disclosures describe methods for administering oxytocin or an oxytocin analog to a mammalian patient in an amount effective to stimulate expression of mammary fluid from a nipple of the patient. The oxytocin or oxytocin analog is preferably administered intranasally and is allowed to reach a target alveolar-ductal tissue of the breast where the oxytocin stimulates myoepithelial contraction of the alveolar-ductal tissue. A mammary fluid collector, preferably a breast pump or fluid collection device such as a solid phase sample collection medium in fluid connection with a breast pump, is then applied to the nipple and receives the expressed breast fluid. Alternatively, the mammary fluid can be expressed and collected without the aid of a breast pump, which may require an increase of oxytocin dosage or lengthening of the post administration time period before breast fluid is fully expressed from the nipple. During or after the mammary fluid expression step, a biological sample is collected from the expressed mammary fluid, which sample may consist of whole mammary fluid, whole cells, cell fragments, cell membranes, selected liquid, cellular or other solid fractions of the mammary fluid, as well as proteins, glycoproteins, peptides, nucleotides (including DNA and RNA polynucleotides) and other like biochemical and molecular constituents of the mammary fluid.

In related aspects of the above-incorporated disclosures, methods are provided for determining the presence or amount of a breast disease marker, preferably a breast cancer marker, in oxytocin-induced biological samples obtained from a mammary organ of a mammalian patient. Samples collected via oxytocin stimulation are assayed to determine the presence and/or amount of the breast disease marker in the sample. Suitable bioassays in this regard include assays to detect known markers of breast infection, such as assays employing immunological or other suitable probes to detect specific antigens and other markers expressed by selected pathogens, including bacterial and viral pathogens. More preferred bioassays detect individual markers or panels of markers of benign breast tumors, pre-cancerous breast disease, and/or breast cancer, such as assays employing immunological or other suitable probes to detect specific antigens and other markers expressed by benign, pre-cancerous and/or cancerous alveolar-ductal cells of the breast.

The foregoing incorporated methods, devices and kits provide highly specific prognostic and treatment related information to facilitate application of the carbetocin treatment and prophylaxis methods and compositions of the instant invention. As components of or adjuncts to the methods and compositions of the invention, the methods and devices set forth above allow identification of patients for which carbetocin treatment is indicated, and allow for close tailoring and monitoring of individual treatments. Notably, carbetocin treatment within the invention, particularly treatment via intranasal administration of carbetocin, may be modified or integrated with additional method steps for breast fluid collection purpose—e.g., as a combinatorial sample collection and treatment method within the present invention. In this context, carbetocin administration within the prophylactic and treatment methods of the invention permits breast fluid sample collection by incidentally stimulating myoepithelial contraction in the mammary ducts of the patient leading to breast fluid expression in susceptible patients at appropriate dosages. Therefore, in conjunction with carbetocin treatment in some patients, breast fluid sample collection and subsequent assays using the methods, kits and devices described above are included as adjuncts to the methods set forth herein below.

As noted above, the methods of the invention involve repeatedly administering a therapeutically effective amount of carbetocin to a patient suffering from breast cancer or presenting with an elevated risk for developing the disease. The carbetocin is formulated with a pharmaceutically acceptable carrier and administered in an amount sufficient to inhibit initiation or growth of breast cancer in the patient. Carbetocin is a long-acting analog of the peptide hormone oxytocin. Oxytocin is normally produced in the pituitary and released into the bloodstream of lactating women in response to suckling. A primary activity of oxytocin is to stimulate contraction of myoepithelial cells in the mammary alveoli and ducts to cause milk ejection (Cobo. *J. Perinat. Med.* 21: 77–85, 1993). Oxytocin is also widely used for stimulating labor in pregnant women, due to its activity of stimulating uterine contractions. Satin et al., *Am. J. Obstet. Gynecol.* 166: 1260–1261, 1992. For these reasons, the pharmacology of oxytocin has been thoroughly investigated, including detailed studies of effective dosages, half-life and potential side effects.

Carbetocin (deamino-1 monocarba-(2-O-methyltyrosine)-oxytocin [d(COMOT)]), like its parent molecule oxytocin, also exhibits uterotonic and milk letdown inducing activities (Atke et al., *Acta Endocrinol.* 115:155–160, 1987; Norstrom et al., *Acta Endocrinol.* 122:566–568, 1990; Hunter et al., *Clin. Pharmacol. Ther.* 52:60–67, 1992; Silcox et al., *Obstet. Gynecol.* 82:456–459, 1993; Vilhardt et al., *Pharmacol. Toxicol.* 81:147–150, 1997; Boucher et al., *J. Perinatology* 18:202–207, 1998, each incorporated herein by reference). However, the half-life of carbetocin is reportedly 4 to 10 times longer than that of oxytocin. This is reflected in substantial prolongation of the uterotonic and milk let-down inducing activities and is attributed to N-terminal desamination and methylene replacement of a 1–6 disulfide bridge in carbetocin rendering the molecule resistant to aminopeptidase and disulfidase cleavage (Hunter et al., *Clin. Pharmacol. Ther.* 52:60–67, 1992, incorporated herein by reference).

The methods and compositions of the invention are also useful for the treatment or alleviation of symptoms of a psychiatric disorder in a mammalian patient, as well as for the prophylaxis of patients at risk for developing a psychiatric disorder. Subject patients for treatment according to the methods of the invention include males and females diagnosed with a psychiatric disorder, such as obsessive compulsive disorder, autism or Prader-Willi syndrome, or patients who have been treated for a known psychiatric disorder, and thus present an elevated risk of recurrence. For example, subject patients having obsessive compulsive disorder can be treated with carbetocin or another long-lasting oxytocin analogue. Subject patients typically have a psychiatric disorder (e.g., autism or Prader-Willi syndrome) characterized by one or more obsessive-compulsive behaviors (e.g., excessive worrying, sexual compulsions and/or compulsive washing and cleaning) can be treated with carbetocin or another long-lasting oxytocin analogue to alleviate the symptoms of the obsessive-compulsive behavior.

Subject patients for prophylactic therapy according to the methods of the invention include males and females who have a family history of a psychiatric disorder, or who have a genetic predisposition for developing the disorder (e.g., have markers indicating elevated risk for development of the disorder). Psychiatric disorder treatment and prevention employing the methods and compositions of the invention may be implemented as an independent treatment program or as a follow-up, adjunct or coordinate treatment regimen for patients suffering from such a disorder.

To facilitate identification of patients for which carbetocin treatment according to the invention is indicated, a variety of screening methods are known and widely used in the art. Patients presenting with symptoms of an existing psychiatric disorder may be identified by conventional psychiatric evaluation methods. To identify patients at risk for developing the psychiatric disorder, various screening methods are available. For example, Prader-Willi syndrome is associated with the chromosome 15q11-13. Thus, genetic screen using markers in this region can be used to identify patients that may be likely to develop this syndrome. Such markers can be useful for determining prognostic and/or treatment-related variables. Prognostic variables are those variables that serve to predict the risk of developing the disease. The utility of specific markers for screening and diagnosis depends on the nature and activity of the marker in question. The presence of certain genetic markers may be predictive of a genetic predisposition for the genetic disorder.

As noted above, for the treatment or prevention of psychiatric disorders, the methods of the invention involve repeatedly administering a therapeutically effective amount of carbetocin to a patient. Carbetocin has been reported as an antagonist to the oxytocin receptor (Engstrom et al., *Eur. J. Pharmacol.* 355:203–10, 1998). Due to carbetocin's reportedly longer half life, high levels of carbetocin can block oxytocin receptors, and thereby reduce binding of oxytocin to its receptor. Thus, administration of high levels of carbetocin can be used to alleviate psychiatric symptoms associated with abnormally elevated oxytocin levels.

The carbetocin is typically formulated with a pharmaceutically acceptable carrier and administered in an therapeutically effective amount, according to the intended use and the desired results. For example, a therapeutically effective amount can be an amount sufficient to inhibit initiation or growth of breast cancer in the patient. As noted elsewhere herein, carbetocin is a long-acting analog of the peptide hormone oxytocin, and the pharmacology of oxytocin has been thoroughly investigated, including detailed studies of effective dosages, half-life and potential side effects.

For use within the present invention, carbetocin preparations are provided for intranasal, intrapulmonary, intramuscular, intravenous, transmucosal or transdermal administration that contain carbetocin in a biologically suitable, liquid or solid carrier. The carbetocin is initially provided in substantially pure form and can be obtained from a variety of commercial providers in the United States and elsewhere. Preferred carbetocin preparations contain between about 0.001 and 50 milligrams per milliliter and preferably about 0.1 to 50 mL of liquid carrier or per gram of solid carrier. Because of the known effects of carbetocin to cause uterine contractions, pregnant women should not be treated by the methods contained herein unless the benefits outweigh the risk of inducing premature labor.

As used herein, a "therapeutically effective amount" of carbetocin is an amount of the compound which, depending on the selected mode, frequency and duration of administration, and the desired results. For example, for the treatment or prevention of breast cancer, a therapeutically effective amount is one that inhibits the occurrence or recurrence of breast cancer in the patient or alleviates one or more symptoms of existing breast cancer in the patient. Effective amounts of carbetocin to inhibit the occurrence or recurrence of breast cancer in a patient are prophylactic dosages preferably administered in small amounts over a prolonged course of preventive therapy to patients at risk of getting breast cancer. Determination of effective dosages in this case is typically based on animal model studies followed up by human clinical trials and is approximated by determining effective dosages that significantly reduce the occurrence or incidence of breast cancer in model patients and administration protocols. Alternatively, effective dosages for patients presenting with existing breast cancer can be determined in the patient or using in vitro or in vivo animal or human treatment models and measuring the amount (reflective of dose, administration mode and frequency) of carbetocin required to significantly inhibit growth or metastatic progression of mammary cells explants, or tumors. The time to pharmacokinetic and clinical steady state following carbetocin administration is readily determined depending on the mode, frequency and duration of administration (e.g. bolus dosage, repeat administration, or steady infusion) (See for example, Newton, *Ann. N.Y. Acad. Sci.* 652: 481–483; Mena, *Neuroendocrinology* 61: 722–730, 1995; Gonser, Arch. *Gynecol. Obstet.* 256: 63–66, 1995; Orhue, Obstet. *Gynecol.* 83: 229–233, 1994; Satin et al., *Am. J. Obstet. Gynecol.,* 166: 1260–1261, 1992; and Satin et al., *Obstet. Gynecol.* 83: 234–238, 1994, each incorporated herein by reference in its entirety). It is therefore a routine matter to determine an appropriate concentration and dose of the carbetocin to administer an effective amount (e.g., intranasally effective, transdermally effective, intravenously effective, or intramuscularly effective) of carbetocin to elicit a desired response.

A therapeutically effective amount of carbetocin for the treatment of a psychiatric disorder is one that, depending on the selected mode, frequency and duration of administration, inhibits the occurrence or recurrence of the psychiatric disorder in the patient or alleviates one or more symptoms of the disorder in the patient. Effective amounts of carbetocin to inhibit the occurrence or recurrence of the psychiatric disorder in a patient are prophylactic dosages preferably administered in small amounts over a prolonged course of preventive therapy to patients at risk of developing the disorder. Determination of effective dosages in this case is typically based on human clinical trials and is approximated by determining effective dosages that significantly reduce the occurrence or incidence of the psychiatric disorder in model patients and administration protocols. The time to pharmacokinetic and clinical steady state following carbetocin administration is readily determined depending on the mode, frequency and duration of administration, as discussed above. It is therefore a routine matter to determine an appropriate concentration and dose of the carbetocin to administer an effective amount (e.g., intranasally effective, transdermally effective, intravenously effective, or intramuscularly effective) of carbetocin to elicit a desired response.

A "therapeutically effective amount" of carbetocin thus refers to an amount that is effective, at dosages and for periods of time necessary, to achieve the desired result for an individual patient. The actual dosage of carbetocin will of course vary according to factors such as the disease state, age, and weight of the individual, and the ability of carbetocin to elicit a desired response in the individual. Dosage regimens may be adjusted to provide an optimum therapeutic response. A therapeutically effective amount is also one in which any toxic or detrimental side effects of the carbetocin are outweighed by therapeutically beneficial effects. A non-limiting range for a therapeutically effective amount of carbetocin is 0.001 μg/kg–10 mg/kg, preferably between about 0.001 and 5 mg/kg, although dosages within this range can be achieved by multiple administrations, e.g., multiple administrations per day, daily or weekly administrations. Per administration, it is desirable to administer at least one-tenth of a microgram of carbetocin, preferably between 10 μg and 5.0 mg. It is to be further noted that dosage values may vary with the severity of the condition to be alleviated. In addition, for any particular subject, specific dosage regimens should be adjusted over time according to the individual need and professional judgment of the person administering or supervising the administration of the carbetocin compositions.

Dosage may be varied by the attending clinician to maintain serum levels at a desired level, for example between 1 and 50 nanomoles of carbetocin per liter. Human dosage necessary to achieve circulating serum levels similar to those achieved in a model rat system under standard conditions tend to be about 30 times the model dosage, although this will vary with the metabolism of individual patients. Dosage should also be adjusted based on the release rate of the administered formulation, e.g., nasal spray versus powder, sustained release oral or injected particles, transdermal formulations, etc. To achieve the same serum concentration level, for example, particles with a release rate of 5 nanomolar (under standard conditions) would be administered at about twice the dosage of particles with a release rate of 10 nanomolar (under standard conditions). A non-limiting range for a therapeutically effective amount of carbetocin is 0.001 μg/kg–10 mg/kg, preferably between about 0.001 mg and 5 mg/kg, although dosages within this range can be achieved by multiple administrations, e.g., multiple administrations per day, daily or weekly administrations. Per administration, it is desirable to administer at least one-tenth of a microgram of carbetocin, preferably between 10 μg and 5.0 mg. In general, a dosage of between about 0.05–250 mg per 50 kg of body weight, more preferably between about 0.1 and 25 mg, may be selected. In unit dosage form (e.g., a unit dosage delivered as a single nasal spray, injection, topical application, etc.), a total amount of carbetocin and/or other long-acting carbetocin analogue(s) is preferably selected to be at least about 0.1 mg, 0.5 mg, 1.0 mg 2.0 mg, 5.0 mg or greater. The dosage selected preferably maintains serum concentration below 50 nanomoles per liter, preferably between 1.0 nanomoles per liter and 10, 15 or 25 nanomoles per liter depending on patient's response.

Therapeutic compositions for administering carbetocin can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

As used herein, "pharmaceutically acceptable carrier" includes any and all solvents, dispersion media, coatings, antibacterial and antifungal agents, isotonic and absorption enhancing or delaying agents, and other excipients or additives that are physiologically compatible. Preferably, the carrier is suitable for intranasal, intravenous, intramuscular, subcutaneous, parenteral, oral, transmucosal or transdermal administration. Depending on the route of administration, the active compound may be coated in a material to protect the compound from the action of acids and other natural conditions which may inactivate the compound.

In certain embodiments of the invention, carbetocin is administered in a time release formulation, for example in a composition which includes a slow release polymer, or by depot injection. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparing such formulations are generally known to those skilled in the art (See, e.g., *Sustained and Controlled Release Drug Delivery Systems*, J. R. Robinson, ed., Marcel Dekker, Inc., New York, 1978, incorporated herein by reference). Particularly preferred formulations include controlled-release compositions such as are known in the art for the administration of leuprolide (trade name: LUPRON®), e.g., microcapsules (U.S. Pat. Nos. 4,652,441 and 4,917,893, each incorporated herein by reference), injectable formulations (U.S. Pat. No. 4,849,228, incorporated herein by reference), lactic acid-glycolic acid copolymers useful in making microcapsules or injectable formulations (U.S. Pat. Nos. 4,677,191 and 4,728,721, each incorporated herein by reference), and sustained-release compositions for water-soluble peptides (U.S. Pat. No. 4,675,189, incorporated herein by reference). A long-term sustained release implant also may be used. These can be readily constructed to deliver therapeutic levels of carbetocin for at least 30 days, preferably 60 days or longer. Long-term sustained release implants are well known to those of ordinary skill in the art and can incorporate some of the absorption delaying components described above. Such implants can be particularly useful in treating solid tumors by placing the implant near or directly within the tumor, thereby affecting localized, high-doses of carbetocin at one or more sites of interest. Such implants can also be useful for treating patients who are unable or otherwise unlikely to self-administer the compound.

In alternate embodiments, carbetocin may be orally or rectally administered (e.g., for treatment or prophylaxis of breast cancer or a psychiatric disorder) with an inert diluent or an assimilable edible carrier. The carbetocin may thus be enclosed in a hard or soft shell gelatin capsule, compressed into tablets, or incorporated directly into the subject's diet. For oral therapeutic administration, carbetocin may be incorporated with excipients and used in the form of ingestible tablets, buccal tablets, troches, capsules, elixirs, suspensions, syrups, wafers, and the like. The percentage of carbetocin in these compositions and preparations may, of course, be varied. The amount of carbetocin in such therapeutically useful compositions is such that a suitable dosage will be obtained.

For oral or rectal administration, carbetocin can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms. Solid delivery vehicles may contain carbetocin in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols. As further forms, one can use plug capsules, e.g., of hard gelatin, as well as dosed soft-gelatin capsules comprising a softener or plasticizer, e.g. glycerine.

Alternatively, liquid dosage forms for delivering carbetocin to mucosal surfaces include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

To administer carbetocin in a stable form within the methods of the invention, it may be necessary to coat the compound with, or co-administer the compound with, a material to prevent its inactivation. In this context carbetocin may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7:27, 1984, incorporated herein by reference). Pharmaceutically acceptable carriers include sterile aqueous solutions or dispersions and sterile powders for the extemporaneous preparation of sterile injectable or aerosol solutions or dispersible powder formulations. The use of such media and agents for pharmaceutically active substances is well known in the art. Except insofar as any conventional media or agent is incompatible with the active compound or yields unacceptable toxic or other adverse side effects, use thereof in the pharmaceutical compositions of the invention is contemplated. In one embodiment, supplementary active compounds, including hormonal therapeutic and chemotherapeutic agents useful against breast cancer, can also be incorporated into the compositions of the invention. In another embodiment, the supplementary active compounds include antidepressants, such as selective serotonin reuptake inhibitors (e.g., fluvoxamine, paroxetine, sertraline and paroxetine) or serotonin reuptake inhibitors (e.g., clomipramine).

In more detailed aspects of the invention, carbetocin is stabilized to extend its effective half-life following delivery to the subject, particularly for extending metabolic persistence in an active state within an extracellular compartment (e.g., in the bloodstream, at a mucosal surface, or within a connective tissue compartment or fluid-filled body cavity). For this purpose, carbetocin and other oxytocin analogues may be modified by chemical means, e.g., chemical conjugation, N-terminal capping, PEGylation, or recombinant means, e.g., site-directed mutagenesis or construction of fusion proteins, or formulated with various stabilizing agents or carriers. Carbetocin can also be modified with other appending groups, such as peptides, or agents facilitating transport across the cell membrane (see, e.g., Letsinger et al., *Proc. Natl. Acad. Sci. USA* 86:6553–6556, 1989; Lemaitre et al., *Proc. Natl. Acad. Sci. USA* 84:648–652, 1987; International Patent Publication WO 88/09810) or blood-brain barrier (see, e.g., International Patent Publication WO 89/10134). Thus stabilized, carbetocin administered as above retains activity (e.g., at least 20%, preferably 50%, 80% or more activity compared to a comparable activity observed for unmodified carbetocin) for an extended period at the intended target site for use as an anti-breast cancer agent or for treating a psychiatric disorder.

Numerous reports in the literature describe the potential advantages of PEGylated proteins, which include their increased resistance to proteolytic degradation, increased plasma half-life, increased solubility and decreased antigenicity and immunogenicity (Nucci et al., *Advanced Drug Deliver Reviews* 6:133–155, 1991; Lu et al., *Int. J. Peptide Protein Res.* 43:127–138, 1994, each incorporated herein by reference). A number of proteins, including L-asparaginase, strepto-kinase, insulin, and interleukin-2 have been conjugated to a poly(ethyleneglycol) (PEG) and evaluated for their altered biochemical properties as therapeutics (see, e.g., Ho et al., *Drug Metabolism and disposition* 14:349–352, 1986; Abuchowski et al., *Prep. Biochem.* 9:205–211, 1979; and Rajagopaian et al., *J. Clin. Invest.* 75:413–419, 1985, each incorporated herein by reference). Although the in vitro biological activities of PEGylated proteins may be decreased, this loss in activity is usually offset by the increased in vivo half-life in the bloodstream (Nucci, et al., *Advanced Drug Deliver Reviews* 6:133–155, 1991, incorporated herein by reference).

Several procedures have been reported for the attachment of PEG to proteins and peptides and their subsequent purification (Abuchowski et al., *J. Biol. Chem.* 252:3582–3586,1977; Beauchamp et al., *Anal. Biochem.* 131:25–33, 1983, each incorporated herein by reference). Lu et al., *Int. J. Peptide Protein Res.* 43:127–138, 1994 describe various technical considerations and compare PEGylation procedures for proteins versus peptides (see also, Katre et al., *Proc. Natl. Acad. Sci. USA* 84:1487–1491, 1987; Becker et al., *Makromol. Chem. Rapid Commun.* 3:217–223, 1982; Mutter et al., *Makromol. Chem. Rapid Commun.* 13:151–157, 1992; Merrifield, R. B., *J. Am. Chem. Soc.* 85:2149–2154, 1993; Lu et al., *Peptide Res.* 6:142–146, 1993; Lee et al., *Bioconjugate Chem.* 10:973–981, 1999; Nucci et al., *Adv. Drug Deliv. Rev.* 6:133–151, 1991; Francis et al., *J. Drug Targeting* 3:321–340, 1996; Zalipsky, S., *Bioconjugate Chem.* 6:150–165, 1995; Clark et al., *J. Biol. Chem.* 271:21969–21977, 1996; Pettit et al., *J. Biol. Chem.* 272:2312–2318, 1997; Delgado et al., *Br. J. Cancer* 73:175–182, 1996; Benhar et al., *Bioconjugate Chem.* 5:321–326, 1994; Benhar et al., *J. Biol. Chem.* 269:13398–13404, 1994; Wang et. al., *Cancer Res.* 53:4588–4594, 1993; Kinstler et al., *Pharm. Res.* 13:996–1002, 1996, Filpula et al., *Exp. Opin. Ther. Patents* 9:231–245, 1999; Pelegrin et al., *Hum. Gene Ther.* 9:2165–2175, 1998, each incorporated herein by reference). Following these and other teachings in the art, the conjugation of carbetocin and other oxytocin analogues with poly (ethyleneglycol) polymers is readily undertaken with the expected result of prolonging circulating life and/or reducing immunogenicity while maintaining an acceptable level of activity of the PEGylated carbetocin derivative.

In addition to PEGylation, carbetocin and other oxytocin analogues can be modified to enhance circulating half-life by shielding the protein via conjugation to other known protecting or stabilizing compounds, or by the creation of fusion proteins with the carbetocin proteins or peptides and other proteins such as immunoglobulin chains. These modifications will decrease the degradation, sequestration or clearance of the carbetocin or other oxytocin analog and result in a longer half-life of the protein, e.g., in the nasal sinus, lung, circulatory system, or synovium. Carbetocin thus modified maintains activity for greater periods compared to unmodified carbetocin, but retains substantial biological activity. Such greater activity can be useful, for example, at a target site of breast cancer treatment for inhibiting breast cancer occurrence and/or progression when administered to a subject. Alternatively, such a modified peptide can be useful to treat psychiatric disorders, or symptoms thereof, that are associated with elevated oxytocin levels.

The therapeutic compositions of the invention typically must be sterile and stable under all conditions of manufacture, storage and use. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like. Prolonged delivery of carbetocin in various compositions of the invention can be brought about by inclusion in the composition of agents delaying absorption, for example, aluminum mono sterate hydrogels and gelatin.

When controlled release formulations of carbetocin are desired, controlled release binders suitable for use in accordance with the invention include any biocompatible controlled-release material which is inert to the active ingredient and which is capable of incorporating the carbetocin. Numerous such materials are known in the art. Preferred controlled-release binders are materials which are metabolized slowly under physiological conditions following their subcutaneous or intramuscular injection in mammals (i.e., in the presence of bodily fluids which exist there). Appropriate binders include but are not limited to biocompatible polymers and copolymers previously used in the art in sustained release formulations. Such biocompatible compounds are non-toxic and inert to surrounding tissues, e.g., following subcutaneous or intramuscular injection, and do not trigger significant adverse effects such as immune response, inflammation, or the like. They are metabolized into metabolic products which are also biocompatible and easily eliminated from the body. For example, a polymeric matrix derived from copolymeric and homopolymeric polyesters having hydrolysable ester linkages may be used. A number of these are known in the art to be biodegradable and to lead to degradation products having no or low toxicity. Typically, such preferred polymers are polyglycolic adds (PGA) and polylactic acids (PLA), poly(DL-lactic acid-co-glycolic acid)(DL PLGA), poly(D-lactic acid-coglycolic acid)(D PLGA) and poly(L-lactic acid-co-glycolic acid)(L PLGA). The preferred ratio for lactic acid and glycolic acid polymers in polyo(lactic acid-co-glycolic acid) is in the range of 100:0 (i.e. pure polylactide) to 50:50. Other useful biodegradable or biodegradable polymers include but are not limited to such polymers as poly(epsilon-caprolactone), poly(epsilon-aprolactone-CO-lactic add), poly(epsilon.-aprolactone-CO-glycolic acid), poly(beta.-hydroxy butyric acid), poly(alkyl-2-cyanoacrilate), hydrogels such as poly(hydroxyethyl methacrylate), polyamides, poly(amino acids) (i.e. L-leucine, glutamic acid, L-aspartic acid and the like), poly (ester urea), poly (2-hydroxyethyl DL-aspartamide), polyacetal polymers, polyorthoesters, polycarbonate, polymaleamides, polysaccharides and copolymers thereof.

In preferred embodiments of the invention, carbetocin is administered by topical delivery to a mucosal surface of the patient, preferably via intranasal delivery in the form of an aerosol spray or powder. According to this aspect of the invention, carbetocin is delivered in an intranasally effective amount, preferably in a selected volume of administered spray or powder, to achieve prophylaxis or treatment of breast cancer or a psychiatric disorder. In related aspects of the invention, novel pharmaceutical compositions are provided for intranasal delivery that incorporate carbetocin in a powder or aqueous formulation for intranasal delivery. Intranasal administration of carbetocin is preferred for a variety of reasons. This method allows self-administration of treatment by patients, provided that sufficient safeguards are in place to control and monitor dosing and side effects. Nasal administration also overcomes certain drawbacks of other administration forms, such as injections, that are painful and expose the patient to possible infections and may present drug bioavailability problems.

Compositions according to the present invention are preferably administered in solution as a nasal spray and may be dispensed as a spray by a variety of methods known to those skilled in the art. Systems for intranasally dispensing liquids as a spray are well known (see, e.g., U.S. Pat. No. 4,511,069, incorporated herein by reference). Preferred nasal spray solutions comprise carbetocin in a liquid carrier that optionally include a nonionic surfactant for enhancing absorption of the drug and one or more buffers or other additives to minimize nasal irritation. In addition, any of the enhancers and other excipients used to delivery peptides across absorptive mucosae can be included (see Sayani, A. P. and Chien, Y. W., *Critical Reviews in Therapeutic Drug Carrier Systems* 13:85–184, 1996, incorporated herein by reference). In some embodiments of the present invention, the nasal spray solution further comprises a propellant. The pH of the nasal spray solution is preferably between pH 3.0 and 8.0.

For intranasal administration, compositions which improve the absorption of nasally administered carbetocin and reduce nasal irritation, especially when used in a chronically administered treatment protocol, are desirable. In this context, the utilization of surface-active agents to enhance absorption of polypeptide therapeutics has been previously demonstrated. For example, Hirai and coworkers (Hirai, et al., *Int. J. Pharmaceutics* 1:173–184, 1981; G.B. Patent specification 1 527 605, each incorporated herein by reference). However, nasal administration of drugs enhanced by surfactants may be accompanied by nasal irritation, including stinging, congestion and rhinorrhea. Thus, compositions which enhance absorption through the nasal mucosa with reduced irritation are desirable.

To achieve this goal, a combination of surfactants may be used. Nonionic surfactants such as nonoxynol-9, laureth-9, poloxamer-124, octoxynol-9 and lauramide DEA are particularly useful in the practice of the present invention. Nonoxynol-9 (N-9) is an ethoxylated alkyl phenol, the polyethyleneoxy condensate of nonylphenol with 9 mols of ethylene oxide. This surfactant has been used in detergent products and is sold under trade names, such as, SURFONIC® N-95 (Jefferson), NEUTRONYX® 600 (Onyx) and IGEPAL® CO-630 (GAF). N-9 is considered to be a hard detergent. N-9 has also been used as a spermatocide (*The Merck Index*, 10th Edition, Entry 6518). To minimize irritation attributed to employment of surfactants, one or more anti-irritant additives are included in the carbetocin solution. In one example, polysorbate-80 has been shown to reduce the irritation caused by intranasally administered drugs where delivery was enhanced by use of a nonionic surfactant (See, e.g., U.S. Pat. No. 5,902,789, issued to Stoltz on May 11, 1999, incorporated herein by reference).

Thus, preferred nasal spray solutions of the present invention comprise carbetocin in solution with a nonionic surfactant that enhances nasal absorption of the drug and polysorbate-80, together with one or more pharmaceutically acceptable carriers. Other therapeutic ingredients, including chemotherapeutic and hormonal therapeutic (e.g., tamoxifen) agents may also be included. Desirably, the formulation should not include oxidizing agents and other substances with which the drug(s) to be administered are known to be incompatible. Formulations according to the present invention suitable for nasal administration of carbetocin conveniently comprise sterile aqueous solutions of carbetocin containing a nonionic surfactant which enhances absorption of the drug and polysorbate-80, which solutions are preferably in the range of pH 3.0 and 8.0. Such formulations may be conveniently prepared by dissolving compositions according to the present invention in water to produce an aqueous solution, and rendering said solution sterile. The formulations may be presented in multi-dose containers, for example in the sealed dispensing system as disclosed in U.S. Pat. No. 4,511,069, incorporated herein by reference.

In preferred embodiments of the invention, a nasal spray solution is provided containing approximately 0.001 and 50 milligrams per milliliter and preferably about 0.1 to 50 mL of liquid carrier or per gram of solid carrier. The solution is administered into the nose with a squeeze bottle or other intranasal delivery device held in the upright position while the patient is in a sitting position. One or two sprays of approximately 0.05 to 0.5 ml of the carbetocin solution per spray are administered into each nostril in a fine mist or aerosol. Approximately 0.1 mL is a preferred spray volume. The number and volume of sprays administered, as well as the concentration of carbetocin in the solution, can be adjusted according to well known pharmacokinetic principles (See for example, Newton, *Ann. N.Y. Acad. Sci.* 652: 481–483; Mena, *Neuroendocrinology* 61: 722–730, 1995; Gorser, *Arch. Gynecol. Obstet.* 256: 63–66, 1995; Orhue, *Obstet. Gynecol.* 83: 229–233, 1994; Satin et al., *Am. J. Obstet. Gynecol.* 166: 1260–1261, 1992; and Satin et al., *Obstet. Gynecol.* 83: 234–238, 1994, each incorporated herein by reference in its entirety) and further in accordance with the examples below to ensure that the amount of carbetocin administered to the patient corresponds to an intranasally effective amount to prevent or treat breast cancer, or the psychiatric disorder, in the patient.

Alternative means of intranasal carbetocin administration are provided by the use of ion exchange resins or adsorbent resin powders as carriers. Use of these materials is also adaptable for carbetocin administration via oral, percutaneous, gastro-intestinal, rectal, or subcutaneous routes. For intranasal use, these materials minimize irritation to the nasal mucosa and deliver carbetocin in a stable form and with efficient absorption. Thus, methods and compositions are provided wherein carbetocin is formulated with an ion exchange resin or an adsorbent resin powder as a carrier which effectively delivers the carbetocin to, and supports its transfer across, the surface of the nasal mucosa for absorption into the general circulation. The method used for compounding carbetocin with the carrier and other related disclosure is provided in U.S. Pat. No. 5,942,242, issued to Muzushima et al. on Aug. 24, 1999 (incorporated herein by reference). Such methods include: (1) preparing a suspension by adding an ion exchange resin or adsorbent resin powder to a vaccine solution or suspension; (2) mixing dried carbetocin with an ion exchange resin or adsorbent resin powder by means of a mortar or ball mill while maintaining an appropriate relative humidity; (3) freeze drying a suspension obtained by step (1); and (4) increasing the homogeneity of a mixture of step (2) by adding an organic solvent such as ethanol.

Ion exchange resins suitable for use in the present invention include: polystyrenes, methacrylic resin, acrylic resins, phenol-formaldehyde resins, cellulose polymers, dextran polymers, and mixtures thereof. Examples of such polymers include, sodium polystyrenesulfonate prepared according to the Pharmacopeia of Japan, calcium polystyrene sulfonate prepared according to the Pharmacopeia of Japan, AMBERLITE® 1RP64, AMBERLITE® CU-SO, AMBERLITE® DP-1, and DOWE® 2, and mixtures thereof, which bear as cation exchange functional groups, sulfonic acid or carboxylic acid, or a salt thereof, e.g., a sodium, potassium, or calcium salt. The anion exchange resins include, for example, quaternary ammonium resin derivatives or, e.g., chloride, salts thereof. Examples of such chloride salts include cholestyramine, AMBERLITE® 1RP67, AMBERLITE® IRA-68, DOWEX® SOw, and mixtures thereof.

Examples of adsorbent resins for use within the invention include styrenedivinylbenzenes, such as: DIAION® HP 10; DIAION® HP20; Sepabead 207; AMBERLITE® XAD2; LEWATIT® 0C103 1; DOLITE® E586 1; methacrylic acid esters, such as DIAION® HP2MG and AMBERLITE® XAD-7; polyethylenes; vinyl chloride resins; amino acid sulfoxides; and mixtures thereof.

To provide an optimal intranasal powder for delivery of carbetocin, a mean particle size of the ion exchange resin or adsorbent resin is not larger than 200$\mu$, preferably 10 to 150$\mu$, and still more preferably 40 to 70$\mu$. The total amount of powdered medicament to be administered into the human nasal cavity as a single dose is preferably approximately 5 to 50 mg, preferably 10 to 30 mg, more preferably 15 to 25 mg. In this case, the total amount is the sum of the amount of carbetocin and carrier as well as any other active ingredients or additives. As for solid medicaments delivered in a liquid suspension (e.g., a carbetocin/resin solid suspended in a liquid carrier), the amount for a single dose is preferably 0.1 to 2.5 ml, preferably 0.2 to 2.0 ml, more preferably 0.3 to 1.5 ml.

To increase both adherence to the nasal mucosa and the stability of nasal powders and solid suspensions, the present invention may include a water-soluble polymer powder, such as: polyacrylic acid or polymethacrylic acids or metal salts, such as sodium salt or potassium salts, thereof, with a mean particle size of 0.5 to 200$\mu$, preferably 20 to 100$\mu$; a water-soluble acrylate polymer such as polyacrylamide, having a molecular weight of 30,000 or greater, preferably 50,000 to 10,000,000; carboxyvinyl polymers, methylcelluloses, ethylcelluloses, hydroxymethylcelluloses, hydroxypropylmethylcelluloses, carboxymethylcelluloses, carboxymethylchitin, polyvinylpyrrolidone, polyvinylalcohols, ester gums, polybutene, synthetic hydroxypropyl-starch, synthetic carboxymethyl-starch, synthetic polyvinylethers, and polyethylene oxide, having an average molecular weight of 20,000 to 9,000,000, and preferably 100,000 to 7,000,000; natural polymers such as hyaluronic acid, sodium alginate, gelatin, gluten, carboxymethyl-starch, hydroxypropyl-starch, gum arabic, mannan, dextran, tragacanth, amylopectin, xanthan gum, locust bean gum, casein, polyvinylethers, and pectin; and mixtures thereof.

In yet additional aspects of the invention, carbetocin and/or other long-acting oxytocin analogues is administered according to the foregoing methods in a coordinate treatment or prophylaxis protocol with a secondary agent. In various preferred embodiments, the secondary agent is an anti-cancer agent. Preferred secondary anti-cancer agents in this context are conventional hormonal and chemotherapeutic treatment agents. In one embodiment, carbetocin is administered coordinately with the anti-estrogen compound tamoxifen to prevent or treat breast cancer. The carbetocin is administered as above, simultaneously or sequentially with administration of raloxifene or tamoxifen, the latter of which is administered in an amount sufficient to independently inhibit initiation or growth of estrogen-dependent breast cancer in the patient.

In another embodiment, the secondary agent is a selective serotonin reuptake inhibitor (SSRI) or serotonin uptake inhibitor. Preferred SSRI's in this context are conventional agents, such as fluvoxamine, paroxetine, sertraline and paroxetine, and preferred SRI's are clomipramine. The carbetocin may be administered coordinately with the SSRI or SRI to prevent or treat breast cancer. The carbetocin is administered as above, simultaneously or sequentially with administration of the SSRI or SRI, the latter of which are administered in an amount sufficient to independently treat, prevent or alleviate symptoms of a psychiatric disorder in the patient.

The instant invention also includes kits, packages and multi-container units containing the above described pharmaceutical compositions, active ingredients, and/or means for administering the same for use in the prevention and treatment of breast cancer, or a psychiatric disorder, as discussed above. Briefly, these kits include a pharmaceutical preparation of carbetocin in a biologically suitable carrier optionally contained in a bulk dispensing or unit or multi-unit dosage form. Optional dispensing means may be provided for administering the carbetocin, preferably including an intranasal spray applicator. Preferred applicators include pressurized aerosol or hand-pump reservoirs preferably equipped with a nozzle for placement in a nostril of the patient and functional to direct a liquid spray of the carbetocin solution therein.

Kits of the invention also optionally include a collecting device for collecting a biological sample from expressed mammary fluid in conjunction with carbetocin treatment as described above. The collecting device may range from a simple fluid reservoir to a solid phase medium that can be directly incorporated into solid phase bioassays, as well as a variety of other breast fluid collection devices and sampling components as described, e.g., in U.S. Pat. No. 5,7998, 266 issued to Quay et al. on Aug. 25, 1998; U.S. patent application Ser. No. 09/027,362 filed by Quay et al. on Feb. 20, 1998; and U.S. patent application Ser. No. 09/435,131, filed by Quay et al. Nov. 5, 1999 (each incorporated herein by reference). In this latter context, an optional breast pump may be provided in the kit that is applicable to a human breast and designed to generate intermittent or sustained negative pressures in an area surrounding the nipple. More preferably, the breast pump serves a dual purpose of applying negative pressure to the breast to facilitate mammary fluid expression from the nipple following carbetocin stimulation, and to provide a reservoir or solid phase collecting device fluidly connected with the breast pump for biological sample collection. In more detailed embodiments of the invention, kits include reagents and/or devices for detecting the presence and/or amount of a breast disease marker in the biological sample, for example an immunological or molecular probe that binds or reacts with a breast cancer marker. The kits may also contain suitable buffers, preservatives such as protease inhibitors, direct or sandwich-type labels for labeling probes, and/or developing reagents for detecting a signal from the label. Thus, a broad selection of therapeutic and diagnostic kits are provided within the invention based on the description herein, including kits that contain specific instructions for carrying out the prophylactic and treatment protocols and associated assays of the invention.

The following examples are offered by way of illustration, not by way of limitation.

In various exemplary embodiments of the invention, the methods and compositions disclosed herein can be used prophylactically to reduce the incidence of breast cancer in patients at elevated risk for developing the disease. In addition, carbetocin therapy can be employed to inhibit recurrence of breast cancer in patients previously treated for the disease, for example as a follow-up therapy for patients treated by surgery and/or conventional chemotherapy. Typically, carbetocin therapy will reduce the incidence or recurrence of breast cancer in test subjects by at least 10%, preferably >20%, and most preferably >30% or more, compared to the incidence or recurrence of disease observed in control subjects. Efficacy in this context can be determined directly by identification and/or quantitation of clinical symptoms of breast cancer in the patient, or by identification and/or quantitation of one or more structural, biochemical or physiological markers correlated with the incidence or occurrence of breast cancer in a subject, as described above. In the latter case, carbetocin therapy will reduce the incidence, frequency or quantitative level of one or more breast cancer markers by at least 10%, preferably >20%, and most preferably >30%, or more, compared to the incidence or recurrence of disease observed in control subjects. Patients for whom prophylactic carbetocin treatment is indicated include individuals presenting with a significant familial history of breast cancer, individuals in relapse from breast cancer as well as individuals who exhibit elevated levels of one or more breast cancer markers identified by the above-described screening methods.

Carbetocin therapy in accordance with the instant invention may also be used for treating existing breast cancers. Preferably, administration of carbetocin will result in a significant reduction in the rate of growth of breast tumors and will often lead to a significant (e.g., at least 5–29%, preferably 30–50% or greater) diminution in size (e.g., as reflected by a decrease in tumor area, volume or weight) of existing cancer or tumor masses in the treated subject compared to non-treated control subjects. In addition, or alternatively, the methods and compositions of the invention will significantly inhibit progression of existing breast cancer tumors to a higher histologic grade and/or from an organ-confined to a metastatic condition.

In other exemplary embodiments of the invention, the methods and compositions disclosed herein can be used prophylactically to reduce the incidence of a psychiatric disorder in patients at increased risk for developing such disorder or behavior. In addition, carbetocin therapy can be employed to inhibit recurrence of a psychiatric disorder. Typically, carbetocin therapy will reduce the incidence or recurrence of such a psychiatric disorder in test subjects by at least 10%, preferably >20%, and most preferably >30% or more, compared to the incidence or recurrence of the psychiatric disorder and/or an obsessive-compulsive behavior observed in control subjects. Efficacy in this context can be determined directly by identification and/or quantitation of clinical symptoms in the patient.

Carbetocin therapy in accordance with the instant invention may also be used for treating existing psychiatric disorders and/or an obsessive-compulsive behaviors. Preferably, administration of carbetocin will result in a significant reduction of the symptoms of the psychiatric disorder and/or an obsessive-compulsive behavior and will often lead to a significant (e.g., at least 5–29%, preferably 30–50% or greater) diminution the frequency or severity of the symptoms in the treated subject compared to non-treated control subjects.

As described above, carbetocin therapy may be effectuated using a variety of delivery routes, administration protocols, and dosages. Preferably, carbetocin is administered intranasally for both prophylactic and treatment purposes. In both instances, repeated, low dose administration of carbetocin is preferred. Metered doses of aerosolized carbetocin are calibrated at 10 percent (10%) constancy of dose and delivered by preferred means of a specially constructed mechanical pump valve (U.S. Pat. No. 4,511,069, incorporated herein by reference). This hand-held delivery device is uniquely nonvented so that sterility of the solution in the aerosol container is maintained indefinitely.

Generally, about 0.1 ml of carbetocin spray solution, for example carbetocin in lactated Ringer's, will constitute a single dose, which preferably contains between about 1 $\mu$g and 5.0 mg of carbetocin. Multiple doses may be administered, for example one or more doses per day. For prophylactic and treatment purposes, a carbetocin dose of at least 1 $\mu$g, preferably at least 5 $\mu$g, more preferably between about 10 $\mu$g to 1 mg or greater, may be administered daily. Greater or more frequent doses may be administered depending on the patient's age, weight, severity of symptoms and the presence or absence of side effects. Prophylactic therapy may be continued indefinitely so long as side effects are absent or remain at an acceptable level. Usually, treatment of existing conditions will be more intensive than prophylactic therapy, i.e., carried out using higher or more frequent doses. Breast cancer treatment in this context will typically continue for at least 3–14 days before a significant reduction in the rate of growth, size or metastatic potential of an existing tumor is effectuated. Thereafter, intensive treatment may be continued for 3–4 weeks up to six months before the therapy may be discontinued, or reduced to a prophylactic dosage level. Carbetocin may be employed as a primary or adjunct therapy before, during or after the patient has been treated by surgery, chemotherapy, radiation or hormonal therapy. Psychiatric disorder treatment in this context will typically continue for at least 1–6 months before a significant reduction in the psychiatric disorder or symptoms thereof is effectuated.

EXAMPLE I

Carbetocin Formulations for Nasal Administration

The following carbetocin nasal formulations exemplify additional formulations provided for use within the methods of the invention. Nasal formulations of carbetocin for animal testing, human clinical trials and commerce are manufactured under current Good Manufacturing Practice (cGMP). The formulations are sterile when manufactured.

Formulation A: A 20 L carbetocin solution for therapeutic use is formulated in a 25 L glass vessel. Eighteen liters of Water for Injection USP are placed in the vessel and under stirring, the following are sequentially added and a solution created:

| | |
|---|---|
| Sodium acetate | 20 g |
| Sodium chloride | 340 mg |
| Chlorobutanol NF | 100 mL |

To the solution is added 20 g of carbetocin with stirring until all of the carbetocin has dissolved. The pH is adjusted to between 3.7 and 4.3 and the batch is transferred to a balance and additional Water for Injection USP is added to complete the formulation. The batch of solution is terminally sterilized by aseptic filtration through a $0.2\mu$ membrane filter system and filled into 5.0 mL glass vials that are closed with a mist activator that discharges 0.1 mL liquid per spray. Between 3600 and 3950 vials are obtained from the batch.

Formulation B: A 20 L carbetocin solution for therapeutic use is formulated in a 25 L glass vessel under an inert atmosphere of nitrogen. Eighteen liters of Water for Injection USP are placed in the vessel and under stirring, the following are sequentially added and a solution created:

| | |
|---|---|
| Chlorobutanol NF | 10 mL |
| Glycerol | 400 mL |
| Benzalkonium chloride | 2 g |
| Sorbitol | 1 kg |

To the solution is added 20 g of carbetocin with stirring until all of the carbetocin has dissolved. The pH is adjusted to between 3.7 and 4.3 with 50 mM citric acid and/or 50 mM sodium phosphate, monobasic and the batch is transferred to a balance and additional Water for Injection USP is added to complete the formulation. The batch of solution is terminally sterilized by aseptic filtration through a $0.2\mu$ membrane filter system and filled into 5.0 mL glass vials that are closed with a mist activator that discharges 0.1 mL liquid per spray.

Formulation C: The benzalkonium of formulation B is substituted with methyl paraben and propyl paraben.

Formulations D, E, and F: Various formulations designated Formulation D can be obtained from formulation A by altering the carbetocin amount from 20 mg per batch to 50 mg, 100 mg, 500 mg and up to 1 kg or more per batch. Various formulations designated Formulation D can be obtained from formulation B by altering the carbetocin amount from 20 mg per batch to 50 mg, 100 mg, 500 mg and up to 1 kg or more per batch. Various formulations designated Formulation F can be obtained from formulation C by altering the carbetocin amount from 20 mg per batch to 50 mg, 100 mg, 500 mg and up to 1 kg or more per batch.

EXAMPLE II

Prevention of Mammary Carcinoma Induced by Dimethylbenz(a)-Anthracene (DMBA) in the Rat by Nasal Administration of Carbetocin To demonstrate the efficacy of the present invention in reducing the incidence of mammary carcinoma in mammalian subjects, intranasal carbetocin is administered as described above to model rat subjects beginning one week before carcinoma is induced in the treated subjects with dimethylbenz(a)anthracene. Female Sprague-Dawley (Crl; CD(SD)Br) rats (obtained from Charles River Canada Inc., St. Constant, Quebec) at 50 to 52 days of age are subjected to intranasal carbetocin administration at stepwise dosages and frequencies. The carbetocin nasal spray solution will contain commercially available carbetocin in 0.1M $NaH_2PO_4$—$H_2O$ buffer, and varying concentrations of polysorbate-80 and nonoxynol-9. For this purpose, stock solutions containing 10:90, 50:50 and 25:75 (wt:wt) polysorbate 80: nonoxynol-9 are prepared and added to the spray solution to a final concentration of 0.1% to 0.7 5% by weight. Nitrous oxide (Union Carbide, N.Y.) is used as a propellant. Formulations A, B, or C of Example I can also be used in these studies. The carbetocin therapy is initiated one week before administration of the DMBA, and animals are divided into separate dosage groups and a control group. Exemplary dosages for test animals range between about 0.01 and 5 mg/kg of carbetocin, exclusive of the selected carrier, administered one or more times daily. Mammary carcinoma is induced in the test subjects by a single intragastric administration of 20 mg of dimethylbenz(a) anthracene (DMBA) (Sigma Chemicals co., St. Louis, Mo.) in 1 ml of corn oil.

Test and control animals are monitored continuously after carbetocin treatment for signs of adverse side effects, including nasal irritation. The subjects are monitored during a period from about 30 to 85 days following administration of DMBA for determining the incidence of tumor development. Using standard methods, the average number of tumors per animal is determined for test groups protected by selected carbetocin dosages and compared with the average number of tumors per animal in the unprotected control group. Tumor number and size, e.g., as measured with calipers, are determined weekly. In accordance with the teachings herein, carbetocin-treated groups will show significantly greater resistance to development of tumors than the unprotected group.

The carbetocin dosing schedule and formulations used in these animal studies, when used in human patients, will also show a significant resistance to the development of tumors compared to untreated or placebo treated control patients.

EXAMPLE III

Treatment of Existing Mammary Carcinoma Induced by DMBA in the Rat by Nasal Administration of Carbetocin The efficacy of carbetocin therapy for treating existing breast cancer is also demonstrated using an accepted model rat system in which carcinoma is induced by DMBA. In this example, tumors are induced in ovariectomized Female Sprague-Dawley rats at 50 to 52 days of age by a single intragastric administration of 20 mg of DMBA in 1 ml of corn oil. In both treatment and control groups, estradiol is used to stimulate tumor growth. Intranasal carbetocin (buffered and with varying concentrations of polysorbate-80 and nonoxynol-9 or using formulations A, B, or C of Example I) is administered as described above to a series of test groups of subjects at stepwise dosages and frequencies. The carbetocin therapy is initiated beginning 30 days after administration of DMBA. Test and control animals are monitored continuously thereafter for adverse side effects and to assess the incidence and extent of tumor development. Using standard methods, tumor number and size are determined weekly for a period of up to six months. In accordance with the teachings herein, carbetocin-treated groups will show significantly lower incidence of tumors and reduced rates of tumor growth.

The carbetocin dosing schedule and formulations used in these animal studies, when used in human patients, will also show a significant lower incidence of tumors and reduced rates of tumor growth compared to untreated or placebo treated control patients.

EXAMPLE IV

Prevention and Treatment of Mammary Carcinoma in SCID Mice Xenografted with Human Mammary Carcinoma Cells by Administration of Carbetocin and by Coordinate Administration of Carbetocin and Tamoxifen Yet another system for demonstrating the efficacy of carbetocin therapy to treat existing breast cancer employs the well known SCID mouse model for human breast cancer intervention. In this example, severe combined immunodeficient (SCID) mice are xenografted with human breast carcinoma cells (e.g., MCF7 or MDA-MB231 cells) that may be estrogen-dependent or estrogen independent. Tumor growth is optionally stimulated with estradiol. Carbetocin is intranasally administered at varying dosages and administration schedules as above to xenografted and control animals, before or after inoculation with the human breast cancer cells. In alternate examples, carbetocin is co-administered with tamoxifen to determine the effects of coordinate carbetocin/tamoxifen therapy for breast cancer prophylaxis and treatment. Coordinate therapy examples may involve stepwise increased dosages of both carbetocin and tamoxifen to different test animals. Alternatively, dosage of each agent may be reciprocally varied, or held stable for one agent and increased or decreased for the other, among different groups of test animals to determine optimal protocols for coordinate therapy.

For tumor induction, SCID mice are inoculated subcutaneously with $5 \times 10^6$ MCF7 or MDA-MB231 cells, after which the inoculated mice rapidly develop xenografted tumors. Beginning one week before or 30 days after inoculation of the human breast cancer cells, carbetocin is administered as described above to a series of test subjects at stepwise dosages and frequencies. Alternatively, tamoxifen may be administered coordinately in a mixture or as a separate formulation with the carbetocin. All mice are monitored daily for health status and are sacrificed when they became moribund, develop tumors which impede their ability to attain food or water, or at the end of 20 weeks when each trial is completed (median survival of control mice inoculated with MDA-MB231 cells is 52 days, and by 20 weeks, most control (xenografted/untreated) mice have died). Using standard methods, tumor number and size are determined weekly throughout the trials. In addition or alternatively, histopathological examinations are conducted on sacrificed animals to evaluate tumor cytology and histologic organization to assess tumor progression and metastatic activity. In both carbetocin-treated and carbetocin/tamoxifen-treated groups significantly lower incidence of tumors and reduced rates or tumor growth and progression are expected.

The effectiveness of carbetocin prophylaxis and treatment in humans correlate well with the results obtained using murine and rat model systems as described above. Based on these results, carbetocin prophylaxis and treatment in humans may be further evaluated and optimized through controlled clinical trials. Patients with a high risk of breast cancer, either based on genetic testing or family history or other criteria, will be recruited to trials designed to test for the prevention or delay of breast cancer. Patients presenting with breast cancer treatable by the methods of the invention with measurable or otherwise evaluatable tumors will be recruited into trials designed to for treatment of existing cancer. Breast cancer markers as described above which have been shown to be correlated with the risk or extent of disease will also be considered as a basis for including subjects in human clinical trials to evaluate clinically acceptable parameters, e.g., dosage and efficacy, for carbetocin therapy. Tumors in humans will be measured or evaluated before and after treatment by CT scan, MRI scan, ultrasonography or other methods. The criteria for evaluating anti-tumor responses are adopted from the WHO Handbook of Reporting Results of Cancer Treatment, WHO Offset Publication 1979, 49-World Health Organization, Geneva, incorporated herein by reference.

EXAMPLE V

Treatment of Obsessive-Compulsive Behaviors in Patients by Administration of Carbetocin The ability of the oxytocin analog, carbetocin, to alleviate symptoms of obsessive compulsive disorder (OCD) are tested in an 8-week trial. 15 adult OCD patients are recruited. The patents exhibit symptoms of OCD for at least a year, a Yale-Brown Obsessive Compulsive Scale (Y-BOCS) score of greater than or equal to the desired score, and no organic, psychotic, or other primary Axis I disorder. The patients are divided into three groups. The control group continues to receive other psychotropic medications (e.g., SRI or SSRI). One test group receives the psychotropic medication plus carbetocin. For the second test group, other psychotropic medications are discontinued while carbetocin is administered. Carbetocin is administered daily in two intranasal doses. Periodically throughout the trials, the Y-BOCS score of the patient is determined. The criteria for evaluating the success of the treatment are adopted from standard psychiatric evaluation methods.

The invention now having been fully described, it will be apparent that many changes and modifications can be made in accordance with the description above by applying ordinary knowledge and skill in the art without departing from the spirit or scope of the appended claims which are offered by way of illustration and exemplification, not limitation. All publications, patents and patent applications are herein incorporated by reference for all purposes, particularly those pertaining to practice, description and use of the invention.

What is claimed is:

1. A method for treatment of breast cancer in a mammalian patient comprising administering to said patient a therapeutically effective amount of carbetocin in a pharmaceutically acceptable carrier sufficient to inhibit growth of breast cancer in said patient.

2. The method of claim 1, wherein said carbetocin is administered to said patient by a mode of administration selected from intramuscular, intravenous, intranasal, intrapulmonary, subcutaneous, parenteral, oral, or transdermal delivery.

3. The method of claim 2, wherein said carbetocin is administered to said patent intranasally.

4. The method of claim 2, wherein said carbetocin is formulated in said carrier for intranasal or intrapulmonary administration.

5. The method of claim 4, wherein said carbetocin is formulated in a powder or aqueous formulation for intranasal delivery.

6. The method of claims 5, wherein said carbetocin is combined in an aqueous formulation with one or more excipients selected from the group consisting of nonoxynol-9, laureth-9, poloxamer-124, octoxynol-9, lauramide DEA, chlorobutanol, glycerol, citric acid, sodium acetate for intranasal delivery.

7. The method of claim 5, wherein said carbetocin is formulated with a nonionic surfactant and polysorbate-80 in an aqueous formulation for intranasal delivery.

8. The method of claim 1, wherein said carbetocin is administered in a dose of at least one microgram.

9. The method of claim 1, wherein said carbetocin is administered daily in an intranasal formulation.

10. The method of claim 1, further comprising administering tamoxifen and/or raloxifene to said patient in an amount sufficient to inhibit growth of estrogen-dependent breast cancer in said patient.

11. The method of claim 10, wherein said carbetocin and said tamoxifen and/or raloxifene are administered simultaneously as a mixture.

* * * * *